United States Patent

Miyachi et al.

[11] Patent Number: 6,103,747
[45] Date of Patent: Aug. 15, 2000

[54] IMIDAZOLE DERIVATIVES AND PROCESS FOR PREPARING THE SAME

[75] Inventors: Hiroyuki Miyachi, Kazo; Kei Okazaki; Hiromi Kiyota, both of Nogi-machi; Mitsuru Segawa, Omiya, all of Japan

[73] Assignee: Kyorin Pharmaceutical Co., Ltd., Tokyo, Japan

[21] Appl. No.: 09/313,979

[22] Filed: May 19, 1999

Related U.S. Application Data

[62] Division of application No. 08/652,551, filed as application No. PCT/JP94/02021, Dec. 1, 1994, Pat. No. 5,932,607.

[30] Foreign Application Priority Data

Dec. 10, 1993 [JP] Japan ................................. 5-341467
Nov. 29, 1994 [JP] Japan ................................. 6-319355

[51] Int. Cl.⁷ ...................... A61K 31/415; C07D 233/60; C07D 233/61
[52] U.S. Cl. ...................... 514/399; 514/400; 548/338.1; 548/341.5
[58] Field of Search .............................. 548/338.1, 341.5; 514/399, 400

[56] References Cited

U.S. PATENT DOCUMENTS

| | | |
|---|---|---|
| 4,073,921 | 2/1978 | Miller et al. |
| 4,225,723 | 9/1980 | Miller et al. |
| 4,320,134 | 3/1982 | Iizuka et al. |
| 4,605,661 | 8/1986 | Hirsch et al. |
| 4,923,865 | 5/1990 | Cossement et al. |

FOREIGN PATENT DOCUMENTS

| | | |
|---|---|---|
| 54-112862 | 9/1979 | Japan. |
| 54-163573 | 12/1979 | Japan. |
| 55-162777 | 12/1980 | Japan. |
| 57-56464 | 4/1982 | Japan. |
| 61-12670 | 1/1986 | Japan. |

OTHER PUBLICATIONS

Carl Kaiser et al., "Synthesis and Antimuscarinic Properties of Some N–Substituted 5–(Aminomethyl)–3,3–Diphenyl–2(3H)–Furanones", J. Med. Chem., vol. 35, pp. 4415–4424, 1992.

Donald J. Cram et al., "Organic Chemistry", McGraw–Hill Book Company, 2nd Edition, pp. 565–567, 1964.

*Primary Examiner*—Patricia L. Morris
*Attorney, Agent, or Firm*—Oblon, Spivak, McClelland, Maier & Neustadt, P.C.

[57] ABSTRACT

The invention relates to the imidazole derivatives as selective antagonistic substances against muscarinic acetylcholine and provides imidazole derivatives represented by a general formula (1) or (2)

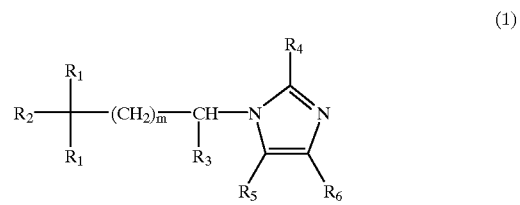

(1)

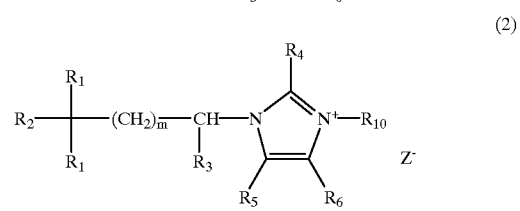

(2)

[wherein $R_1$ is a phenyl group which may have substituent or thienyl group, $R_2$ is a cyano group, a carboxyl group, $CONR_7R_8$ group (wherein $R_7$ and $R_8$ each independently represent hydrogen atom or lower alkyl group, or $R_7$ and $R_8$ may form a ring by alkylene chain which may contain hetero atom) or $COOR_9$ group (wherein $R_9$ is a lower alkyl group), $R_3$ is a hydrogen atom or lower alkyl group, $R_4$, $R_5$ and $R_6$ each independently represent hydrogen atom, lower alkyl group which may have substituent or cycloalkyl groups, or may form a condensed ring at the positions of $R_5$ and $R_6$ with benzene ring, $R_{10}$ is a lower alkyl group or an aralkyl group which may have substituent, m is an integer from 1 to 6, and z is a halogen atom].

3 Claims, No Drawings

IMIDAZOLE DERIVATIVES AND PROCESS FOR PREPARING THE SAME

This application is a Division of application Ser. No. 08/652,551 Filed on Jun. 10, 1996, now U.S. Pat. No. 5,932,607, issued Aug. 3, 1999, which was filed as International Application No. PCT/JP94/02021 filed Dec. 1, 1994.

TECHNICAL FIELD

The present invention relates to therapeutic agents, which are novel imidazole derivatives, and is particularly concerned to imidazole derivatives being anticholinergic agents, especially selective antagonists against muscarinic acetylcholine receptor, process for preparing the same, and pharmaceutical compositions comprising them.

BACKGROUND TECHNOLOGIES

The anticholinergic agents exhibit anticonvulsant action and antisecretory action and have usefulness as the therapeutic agents for functional disorders of intestine, bladder, etc. At present, alkaloids such as atropine, aminoalkanol esters such as oxybutynin and propantheline bromide, their quaternary ammonium salts and the like have been known as the anticholinergic agents, and they are blocking agents for muscarinic acetylcholine receptor. However, because of their poor selectivity among organs in the antagonistic action, the side effects are caused and has posed problems. Therefore, the development of highly selective anticholinergic drug is desired in clinic.

Though, there is a report on 5-[1-(imidazole)methyl]-3,3-disubstituted-2(3H)-furanone derivatives as antagonists against muscarinic acetylcholine receptor, having imidazole group as a substituent, (Japanese Unexamined Patent Publication No. Hei 4-103581), these compounds are different from the inventive compounds in the structure, and yet they don't have adequate activity to satisfy.

The invention provides drugs having higher selectivity and more potent antagonistic activity on muscarinic acetylcholine receptor on smooth muscle than muscarinic acetylcholine receptor on heart.

DISCLOSURE OF THE INVENTION

The inventors had focused on imidazole derivatives for the purpose aforementioned. As a result of diligent studies, so have found that imidazole derivatives represented by the general formula (1)

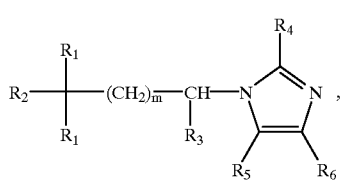

(1)

[wherein $R_1$ is a phenyl group which may have substituent or thienyl group, $R_2$ is a cyano group; a carboxyl group; a $CONR_7R_8$ group (wherein $R_7$ and $R_8$ each independently represent hydrogen atom or lower alkyl group, or $R_7$ and $R_8$ may form a ring by alkylene chain which may contain hetero atom) or a $COOR_9$ group (wherein $R_9$ is a lower alkyl group), $R_3$ is a hydrogen atom or a lower alkyl group, $R_4$, $R_5$ and $R_6$ each independently represent hydrogen atom, lower alkyl group which may have substituent or cycloalkyl groups, or may form a condensed ring at the positions of $R_5$ and $R_6$ with benzene ring, and m is an integer from 1 to 6], or a general formula (2)

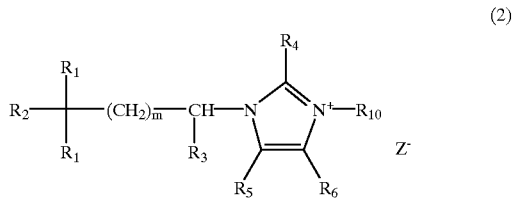

(2)

[wherein $R_1$ is a phenyl group which may have substituent or a thienyl group, $R_2$ is a cyano group, a carboxyl group, a $CONR_7R_8$ group (wherein $R_7$ and $R_8$ each independently represent hydrogen atom or lower alkyl group, or $R_7$ and $R_8$ may form a ring by alkylene chain which may contain hetero atom) or $COOR_9$ group (wherein $R_9$ is a lower alkyl group), $R_3$ is a hydrogen atom or a lower alkyl group, $R_4$, $R_5$ and $R_6$ each independently represent hydrogen atom, lower alkyl group which may have substituent or cycloalkyl group, or may form a condensed ring at the positions of $R_5$ and $R_6$ with benzene ring, $R_{10}$ is a lower alkyl group or an aralkyl group which may have substituent, m is an integer from 1 to 6, and z is a halogen atom], have potent anticholinergic activity, especially selective and potent antagonistic activity on muscarine receptor of smooth muscles of alimentary canal, trachea, bladder, etc., and have brought the invention to completion.

By this reason, the inventive compounds are useful for the treatment of motility disorders of alimentary canal such as irritable bowel syndrome, diverticulum disease, functional diarrhea, esophageal achalasia and cardiospasm, treatment of biliary and urethral spasms, urinary incontinence, etc, treatment of chronic respiratory obstructive diseases, and the like.

The term "substituents" applied to phenyl group shown in the invention indicates halogen, lower alkyl group, lower alkoxy group, nitro group, phenyl group, etc. The term "halogens" indicate fluorine, chlorine, bromine and iodine.

For the "lower alkyl groups" indicate straight or branched chain with the number of carbons from 1 to 6, such as methyl, ethyl and isopropyl.

The term "lower alkoxy groups" indicate ones with straight chain or branched alkyl group with the number of carbons from 1 to 6 bonded to oxygen atom, such as methoxy group, ethoxy group and isopropoxy group.

The term "substituents of lower alkyl group" indicate halogen, lower alkoxy group, hydroxyl group, phenyl group, etc.

The term "cycloalkyl groups" indicate alicyclic hydrocarbons with the number of carbons from 3 to 8, such as cyclopropyl and cyclohexyl.

The term "aralkyl groups" indicate ones with straight chain or branched alkylene group with the number of carbons from 1 to 6 bonded to phenyl group which may have substituent, such as benzyl and phenylethyl.

The term "hetero atoms" indicate oxygen atom, sulfur atom and nitrogen atom.

In the invention, compounds represented by a general formula (3)

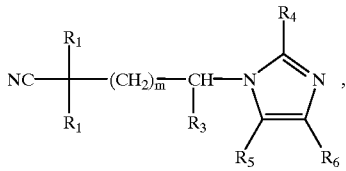
(3)

[wherein $R_1$, $R_3$, $R_4$, $R_5$, $R_6$ and m are as defined above], may be prepared by reacting compounds represented by a general formula (4)

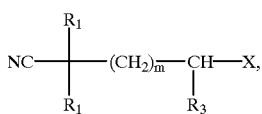
(4)

[wherein, $R_1$, $R_3$ and m are as defined above, and X is a leaving group], with compounds represented by a general formula (5)

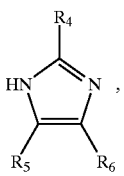
(5)

[wherein $R_4$, $R_5$ and $R_6$ are as defined above], preferably in the presence of base.

Here, the term "leaving group" indicate halogen, aliphatic sulfonyloxy group such as methanesulfonyloxy group, arylsulfonyloxy group such as toluenesulfonyloxy group or the like.

The reaction can be carried out at 0 to 200° C., preferably at 60 to 150° C. in an organic solvent such as dimethylformamide, N-methylpyrrolidone, N,N'-dimethylimidazolidinone, dimethyl sulfoxide or xylene in the presence of inorganic base such as sodium hydroxide, potassium hydroxide, calcium hydroxide, sodium carbonate or potassium carbonate or organic base such as triethylamine or pyridine.

Moreover, in the invention, compounds represented by a general formula (6)

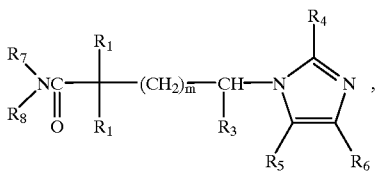
(6)

[wherein $R_1$, $R_3$, $R_4$, $R_5$, $R_6$, $R_7$, $R_8$ and m are as defined above], may be prepared by reacting compounds represented by a general formula (7)

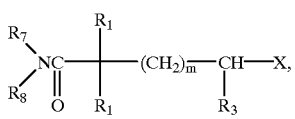
(7)

[wherein $R_1$, $R_3$, $R_7$, $R_8$ and m are as defined above, and X is a leaving group], with compounds represented by the general formula (5)

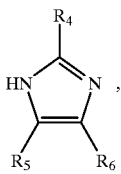
(5)

[wherein $R_4$, $R_5$ and $R_6$ are as defined above], preferably in the presence of base.

The reaction can be carried out at 0 to 200° C., preferably at 60 to 150° C. in an organic solvent such as dimethylformamide, N-methylpyrrolidone, N,N'-dimethylimidazolidinone, dimethyl sulfoxide or xylene in the presence of inorganic base such as alkali metal hydroxide such as sodium hydroxide or potassium hydroxide, metal carbonate such as sodium carbonate or potassium carbonate or organic base such as triethylamine or pyridine.

Furthermore, in the invention, compounds represented by a general formula (8)

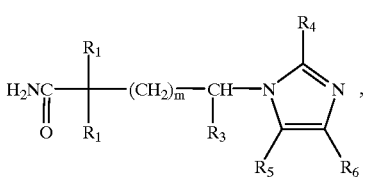
(8)

[wherein $R_1$, $R_3$, $R_4$, $R_5$, $R_6$ and m are as defined above], may be prepared by hydrolysis of compounds represented by the general formula (3)

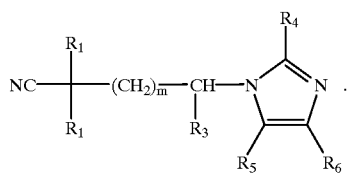
(3)

[wherein $R_1$, $R_3$, $R_4$, $R_5$, $R_6$ and m are as defined above].

The reaction may be carried out at 0 to 150° C., preferably at 100 to 150° C. in a aqueous acidic solution of sulfuric acid or polyphosphoric acid and the like or aqueous alkaline solution of sodium hydroxide or potassium hydroxide and the like.

Still more, in the invention, compounds represented by a general formula (9)

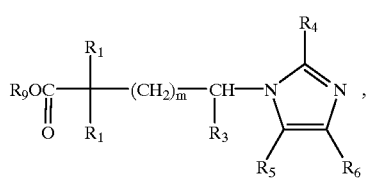
(9)

[wherein $R_1$, $R_3$, $R_4$, $R_5$, $R_6$, $R_9$ and m are as defined above], can be prepared by alcoholysis of compounds represented by the general formula (3)

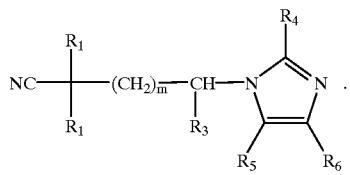
(3)

[wherein $R_1$, $R_3$, $R_4$, $R_5$, $R_6$ and m are as defined above].

The reaction may be carried out at 0 to 150° C., preferably at 100 to 150° C. in aqueous alcohol in the presence of inorganic acid such as sulfuric acid or organic acid such as p-toluenesulfonic acid.

Still more, compounds represented by a general formula (10)

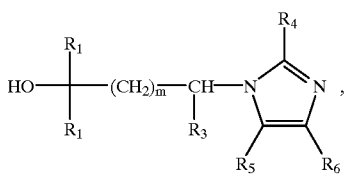
(10)

[wherein $R_1$, $R_3$, $R_4$, $R_5$ $R_6$ and m are as defined above], may be prepared by reacting compounds represented by a general formula (11)

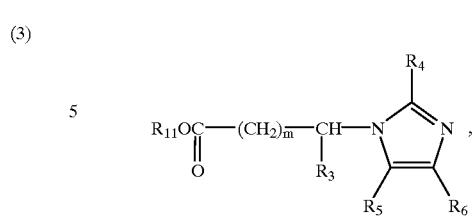
(11)

[wherein $R_3$, $R_4$, $R_5$, $R_6$ and m are as defined above, and $R_{11}$ is a lower alkyl group], with compounds represented by a general formula (12)

$R_1$—Y  (12)

[wherein $R_1$ is as defined above, and Y is lithium or magnesium halogenide], under an inert gas.

The reaction may be carried out at −78 to 30° C. in anhydrous tetrahydrofuran or ether.

Still more, compounds represented by the general formula (2)

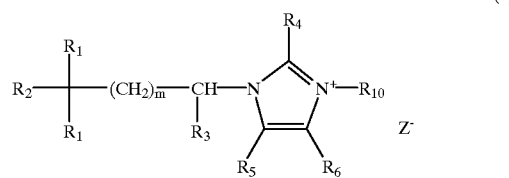
(2)

[wherein $R_1$, $R_2$, $R_3$, $R_4$, $R_5$, $R_6$ $R_{10}$ and m are as defined above, and Z is a halogen atom], may be prepared by reacting compounds represented by the general formula (1)

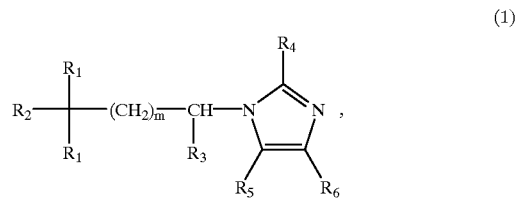
(1)

[wherein $R_1$, $R_2$, $R_3$, $R_4$, $R_5$, $R_6$ and m are as defined above], with compounds represented by a general formula (13)

$R_{10}$—Z  (13)

[wherein $R_{10}$ and Z are as defined above],

The reaction can be carried out at 0 to 100° C. in an organic solvent such as acetone, ethanol, acetonitrile or dimethylformamide.

In the case of the inventive imidazole derivatives containing one or more asymmetric carbons, there will exist optical isomers. The invention includes these isomers and mixtures.

The novel compounds of the invention can be formed to acid addition salts with pharmaceutically acceptable inorganic acids, for example, hydrochloric acid, sulfuric acid, hydrobromic acid and phosphoric acid, or organic acids, for example, maleic acid, fumaric acid, acetic acid, oxalic acid, tartaric acid, benzenesulfonic acid, and the like, by conventional methods.

The inventive novel compounds can be administered orally in the form of tablets, capsules, granules, powders, inhalants, syrups or the like, or can be administered by injections or suppositories or the like.

BEST EMBODIMENT FOR PUTTING THE INVENTION INTO PRACTICE

In following, the invention will be illustrated in detail based on the examples.

Melting point: 157–158.5° C.

Elemental analysis (%): As $C_{20}H_{19}N_3 \cdot HCl \cdot H_2O$. Calculated C: 67.50; H: 6.23; N: 11.81. Observed C: 67.55; H: 6.21; N: 11.99.

$^1$H-NMR (CDCl$_3$, δ), 7.35–7.42 (10H, m), 6.90 (1H, s), 6.77 (1H, s), 3.90–3.94 (2H, m), 2.75–2.79 (2H, m), 2.25 (3H, s).

Examples 2 through 10

According to the process in Example 1, following compounds were prepared (Table 1).

TABLE 1

| Example | $R_4$ | $R_5$ | $R_6$ | m | Salt | Melting point(° C.) (Boiling point) | Composition formula | Elemental analysis(%) Calculated/analyzed | | |
|---|---|---|---|---|---|---|---|---|---|---|
| 2 | $C_2H_5$ | H | H | 1 | HCl | 140–141.5 | $C_{21}H_{21}N_3 \cdot HCl \cdot \frac{1}{5}H_2O$ | C: 70.95 70.80 | H: 6.35 6.45 | N: 11.82 11.98 |
| 3 | i $C_3H_7$ | H | H | 1 |  | (230) 0.4 mmHg | $C_{22}H_{23}N_3 \cdot \frac{1}{5}H_2O$ | C: 79.34 79.47 | H: 7.08 7.04 | N: 12.62 11.57 |
| 4 | H | H | H | 1 | — | (220) 0.4 mmHg | $C_{19}H_{17}N_3 \cdot \frac{1}{5}H_2O$ | C: 78.43 78.66 | H: 6.03 6.20 | N: 14.44 14.23 |
| 5 | H | $CH_3$ | $CH_3$ | 1 | HCl | 162–165 | $C_{21}H_{21}N_3 \cdot HCl$ | C: 71.68 71.34 | H: 6.30 6.35 | N: 11.94 11.89 |
| 6 | H | CH=CH | CH=CH | 1 | HCl | 166–169 | $C_{23}H_{19}N_3 \cdot HCl \cdot \frac{1}{10}H_2O$ | C: 73.53 73.44 | H: 5.42 5.57 | N: 11.19 11.16 |
| 7 | $CH_3$ | H | H | 2 |  | 123–124 | $C_{21}H_{21}N_3$ | C: 79.97 80.09 | H: 6.71 6.78 | N: 13.32 13.15 |
| 8 | $CH_3$ | H | H | 3 | HCl | 166–167 | $C_{23}H_{23}N_3 \cdot HCl \cdot \frac{1}{2}H_2O$ | C: 70.48 70.19 | H: 6.72 6.64 | N: 11.21 11.09 |
| 9 | c $C_3H_5$ | H | H | 1 | — | (250) 0.7 mmHg | $C_{22}H_{21}N_3 \cdot \frac{1}{10}H_2O$ | C: 80.26 80.17 | H 6.49 6.56 | N: 12.76 12.67 |
| 10 | $CH_3O\,CH_2$ | H | H | 1 |  | 124–125 | $C_{21}H_{21}N_3O$ | C: 76.11 76.11 | H: 6.39 6.40 | N: 12.68 12.29 |

Example 1

4-(2-Methyl-1-imidazolyl)-2,2-diphenylbutyronitrile.hydrochloride

4-Bromo-2,2-diphenylbutyronitrile (3.00 g, 10.0 mmol), 2-methylimidazole (2.46 g, 30.0 mmol), triethylamine (1.40 ml, 10.0 mmol) and dimethylformamide (50 ml) were mixed and stirred under heat for 30 hours at 150° C. in a sealed tube. The solution was poured into water, and was extracted with benzene. The organic extract was dried over anhydrous sodium sulfate and then concentrated. The residue was purified by silica gel chromatography (elution solvent; dichloromethane:ethanol=10:1) and formed hydrochloric salt with hydrogen chloride-ether solution. Then, this was recrystallized from ethyl acetate to give 2.60 g of title compound as a colorless powder. Yield: 77%.

Example 11

4-(2-Methyl-1-imidazolyl)-2,2-diphenylbutylamide 4-(2-Methyl-1-imidazolyl)-2,2-diphenylbutyronitrile (7.83 g, 26.0 mmol) and 70% sulfuric acid (50 ml) were mixed and stirred for 40 minutes at 140 to 150° C. The solution was made alkaline and extracted with a mixed solvent (5:1) of chloroform with ethanol. The organic extract was dried over anhydrous sodium sulfate and then concentrated. The residue was recrystallized from ethyl acetate-ethanol to give 2.02 g of title compound as colorless needle-like crystals. Yield: 32%

Melting point: 189–190° C.

Elemental analysis (%): As $C_{20}H_{21}N_3O$. Calculated C: 75.21; H: 6.63; N: 13.16. Observed C: 74.98; H: 6.80; N: 13.00.

$^1$H-NMR (CDCl$_3$, δ), 7.31–7.42 (10H, m), 6.85 (1H, s), 6.73 (1H, s), 5.49 (1H, s), 5.33 (1H, s), 3.77–3.82 (2H, m), 2.69–2.74 (2H, m), 2.23 (3H, s).

Examples 12 through 20

According to the process in Example 11, following compounds were prepared (Table 2).

acetate-ethanol to give 0.35 g of title compound as pale yellow needle-like crystals. Yield: 99%

Melting point: 238–239° C.

Elemental analysis (%): As C$_{23}$H$_{28}$IN$_3$O. Calculated C: 56.45; H: 5.77; N: 8.59. Observed C; 56.35; H: 5.64; N: 8.73.

TABLE 2

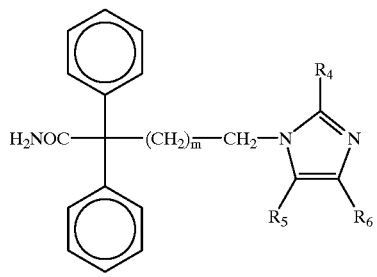

| Example | R$_4$ | R$_5$ | R$_6$ | m | Melting point(° C.) | Composition formula | Elemental analysis(%) Calculated/analyzed | | |
|---|---|---|---|---|---|---|---|---|---|
| 12 | C$_2$H$_5$ | H | H | 1 | 144 146 | C$_{21}$H$_{23}$N$_3$O | C: 75.65 75.42 | H: 6.95 7.08 | N: 12.60 12.43 |
| 13 | n-C$_3$H$_7$ | H | H | 1 | 150–152 | C$_{22}$H$_{25}$N$_3$O | C: 76.05 75.98 | H: 7.25 7.25 | N: 12.09 12.03 |
| 14 | i-C$_3$H$_7$ | H | H | 1 | 176–178 | C$_{22}$H$_{25}$N$_3$O·$^1/_{10}$H$_2$O | C: 75.66 75.67 | H: 7.27 7.30 | N: 12.03 12.04 |
| 15 | H | H | H | 1 | 172–175 | C$_{19}$H$_{19}$N$_3$O·$^3/_5$H$_2$O | C: 72.17 72.20 | H: 6.44 6.32 | N: 13.29 12.89 |
| 16 | H | CH—CH CH—CH | | 1 | 197 199 | C$_{23}$H$_{21}$N$_3$O·$^1/_5$H$_2$O | C: 75.80 75.90 | H: 6.08 5.95 | N: 11.53 11.27 |
| 17 | H | CH$_3$ | CH$_3$ | 1 | 163 164.5 | C$_{21}$H$_{23}$N$_3$O | C: 75.65 75.37 | H: 6.95 7.05 | N: 12.60 12.43 |
| 18 | H | C$_2$H$_5$ | C$_2$H$_5$ | 1 | 194–196 | C$_{23}$H$_{27}$N$_3$O | C: 76.42 76.25 | H: 7.53 7.64 | N: 11.62 11.48 |
| 19 | CH$_3$ | H | H | 3 | 154–156 | C$_{22}$H$_{25}$N$_3$O | C: 76.05 75.96 | H: 7.25 7.22 | N: 12.09 11.93 |
| 20 | t-C$_4$H$_9$ | H | H | 1 | 136–138 | C$_{23}$H$_{27}$N$_3$O·$^1/_2$H$_2$O | C: 74.56 74.60 | H: 7.62 7.46 | N: 11.34 11.10 |

Example 21

4-(2-Isopropyl-3-methyl-1-imidazolyl)-2,2-diphenylbutylamide.iodide

A mixture of 4-(2-isopropyl-1-imidazolyl)-2,2-diphenylbutylamide (250 mg, 0.720 mmol), methyl iodide (5.0 ml), acetone (100 ml) and ethanol (1.0 ml) was stirred under heat for 10 hours in a sealed tube. After the solution was concentrated, the residue was recrystallized from ethyl $^1$H-NMR (d$_6$-DMSO, δ), 7.64 (1H, s), 7.61 (1H, s), 7.46 (1H, s), 7.31–7.43 (10H, m), 6.88 (1H, s), 3.81–3.88 (5H, m), 3.24–3.30 (1H, m), 2.73–2.78 (2H, m), 1.16 (6H, d, J=7.3Hz).

Examples 22 through 26

According to the process in Example 21, following compounds were synthesized (Table 3).

TABLE 3

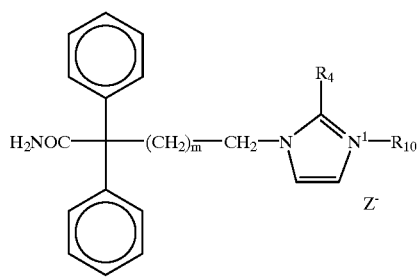

| Example | $R_4$ | $R_{10}$ | m | z | Melting point(° C.) | Composition formula | Elemental analysis(%) Calculated/analyzed | | |
|---|---|---|---|---|---|---|---|---|---|
| 22 | $CH_3$ | $CH_3$ | 1 | 1 | 234–236 | $C_{21}H_{24}IN_3O \cdot \frac{1}{5}H_2O$ | C: 54.25 54.02 | H: 5.29 5.30 | N: 9.04 9.00 |
| 23 | $CH_3$ | $C_2H_5$ | 1 | 1 | 189–192 | $C_{22}H_{26}IN_3O \cdot \frac{3}{5}H_2O$ | C: 54.35 54.54 | H: 5.64 5.78 | N: 8.64 8.34 |
| 24 | $CH_3$ | $CH_2-\text{C}_6H_5$ | 1 | Br | 230 232 | $C_{27}H_{28}BrN_3O$ | C: 66.12 66.41 | H: 5.75 5.86 | N: 8.57 8.68 |
| 25 | $C_2H_5$ | $CH_3$ | 1 | 1 | 229–230.5 | $C_{22}H_{26}IN_3O$ | C: 55.59 55.32 | H: 5.51 5.51 | N: 8.84 8.94 |
| 26 | n $C_3H_7$ | $CH_3$ | 1 | 1 | 215 216 | $C_{23}H_{28}IN_3O$ | C: 56.45 56.69 | H: 5.77 5.83 | N: 8.59 8.89 |

Example 27

3-(2-Methyl-1-imidazolyl)-1,1-diphenylpropanol

In a 200 ml two-neck flask, under an atmosphere of argon, a solution of ethyl 3-(2-methyl-1-imidazolyl)propionate (3.37 g, 18.5 mmol) in anhydrous tetrahydrofuran was added to 50 ml of 1.8M phenyllithium solution at 0° C. After stirred for 3.5 hours at 10° C., the mixture was allowed to stand overnight at room temperature. The solution was poured into water, which was extracted with ethyl acetate. The organic extract was washed with saturated saline solution and dried over anhydrous sodium sulfate, followed by concentration. The residue was purified by silica gel chromatography (elution solvent; ethyl acetate-ethanol=10:1) and then recrystallized from n-hexane-ethyl acetate. This was further recrystallized from ethanol-benzene to give 320 mg of title compound as white needle-like crystals. Yield: 6%

Melting point: 212–214° C.

Elemental analysis (%): As $C_{19}H_{20}N_2O \cdot \frac{1}{10}H_2O$. Calculated C: 77.57; H: 6.92; N: 9.52. Observed C: 77.66; H: 6.87; N: 9.24.

$^1$H-NMR (CDCl$_3$, δ), 7.22–7.44 (10H, m), 6.80 (1H, s), 6.72 (1H, 2), 3.79–3.84 (2H, m), 2.90 (1H, brs), 2.64–2.69 (2H, m), 2.18 (3H, s).

Example 28

3-(2-Methyl-1-imidazolyl)-1,1-diphenylbutanol

Similarly to Example 24, except that 3.60 g (18.3 mmol) of ethyl 3-(2-methyl-1-imidazolyl)butyrate was used in place of ethyl 3-(2-methyl-1-imidazolyl)propionate, 600 mg of title compound were obtained as white cyrstals. Yield: 11%

Melting point: 168–169° C.

Elemental analysis (%): As $C_{20}H_{22}N_2O \cdot \frac{1}{5}H_2O$. Calculated C: 77.49; H: 7.28; N: 9.04. Observed C: 77.21; H: 7.18; N: 8.90.

$^1$H-NMR (CDCl$_3$, δ), 7.19–7.42 (10H, m), 6.87 (1H, d, J=2.0Hz), 6.85 (1H, s), 4.25 (1H, sextet, J=6.2Hz), 2.75 (2H, d, J=5.9Hz), 2.52 (1H, brs), 2.00 (3H, s), 1.34 (3H, d, J=6.9Hz).

Example 29

According to the process in Example 1, following compound was synthesized (Table 4).

TABLE 4

$$NC-\underset{R_1}{\overset{R_1}{C}}-(CH_2)_{\overline{m}}-CH_2-N\underset{R_5\quad R_6}{\overset{R_4}{\diagup\diagdown}}$$

| Example | $R_1$ | $R_4$ | $R_5$ | $R_6$ | m | Melting point(° C.) (Boiling point) | Composition formula | Elemental analysis(%) Calculated/analyzed | | |
|---|---|---|---|---|---|---|---|---|---|---|
| 27 | F-C$_6$H$_4$- | $CH_3$ | H | H | 1 | (240) 0.8 mmHg | $C_{20}H_{17}F_2N_3 \cdot \frac{1}{20}H_2O$ | C: 71.01 71.39 | H: 5.10 5.50 | N: 12.42 12.35 |

Examples 30 through 33

According to the process in Example 11, following compounds were synthesized (Table 5).

TABLE 5

$$H_2NOC-\underset{R_1}{\overset{R_1}{C}}-(CH_2)_{\overline{m}}-\underset{R_1}{\overset{}{CH}}-\underset{R_5}{\overset{R_4}{N}}\underset{R_6}{\overset{}{N}}$$

| Example | $R_1$ | $R_3$ | $R_4$ | $R_5$ | $R_6$ | m | Melting point(° C.) | Composition formula | Elemental analysis Calculated/analyzed | | |
|---|---|---|---|---|---|---|---|---|---|---|---|
| 30 | 4-F-phenyl | H | $CH_3$ | H | H | 1 | 206–207.5 | $C_{20}H_{19}F_2N_3O$ | C: 67.59 / 67.23 | H: 5.39 / 5.55 | N: 11.82 / 11.63 |
| 31 | phenyl | H | H | n $C_3H_7$ | n $C_3H_7$ | 1 | 147 148 | $C_{25}H_{31}N_3O \cdot \frac{1}{3}H_2O$ | C: 76.38 / 76.28 | H: 8.05 / 7.79 | N: 10.69 / 10.69 |
| 32 | phenyl | H | $CH_3$ | H | H | 4 | 159–151 | $C_{23}H_{27}N_3O$ | C: 76.42 / 76.29 | H: 7.53 / 7.53 | N: 11.62 / 11.55 |
| 33 | phenyl | $CH_3$ | $CH_3$ | H | H | 1 | 148 150 | $C_{21}H_{23}N_3O$ | C: 75.65 / 75.48 | H: 6.95 / 7.16 | N: 12.60 / 12.50 |

Examples 34 through 53

According to the process in Example 21, following compounds were synthesized (Table 6, Table 7).

TABLE 6

$$H_2NOC-\underset{\text{(diphenyl)}}{C}-(CH_2)_{\overline{m}}-CH_2-\underset{}{\overset{R_4}{N}}\underset{Z^-}{\overset{}{N^+-R^{10}}}$$

| Example | $R_4$ | $R_{10}$ | m | z | Melting point(° C.) | Composition formula | Elemental analysis Calculated/analyzed | | |
|---|---|---|---|---|---|---|---|---|---|
| 34 | $CH_3$ | n-$C_3H_7$ | 1 | I | 173 175 | $C_{23}H_{28}IN_3O \cdot \frac{1}{3}H_2O$ | C: 56.04 / 55.89 | H: 5.81 / 5.68 | N: 8.52 / 8.51 |
| 35 | $CH_3$ | n-$C_4H_9$ | 1 | I | 164 166 | $C_{24}H_{30}IN_3O$ | C: 57.26 / 57.08 | H: 6.01 / 5.94 | N: 8.35 / 8.23 |
| 36 | $CH_3$ | 2-Cl-benzyl ($CH_2$-$C_6H_4$-Cl) | 1 | Br | 198–199 | $C_{27}H_{27}BrClN_3O \cdot \frac{1}{3}H_2O$ | C: 61.36 / 61.16 | H: 5.23 / 5.08 | N: 7.95 / 7.91 |

TABLE 6-continued
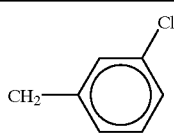
| Example | $R_4$ | $R_{10}$ | m | z | Melting point(° C.) | Composition formula | Elemental analysis Calculated/analyzed | | |
|---|---|---|---|---|---|---|---|---|---|
| 37 | $CH_3$ |  | 1 | Br | 221–222 | $C_{27}H_{27}BrClN_3O$ | C: 61.78 / 61.54 | H: 5.19 / 5.32 | N: 8.01 / 7.95 |
| 38 | $CH_3$ | 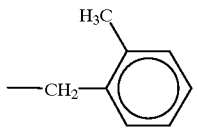 | 1 | Br | 133–135 | $C_{27}H_{27}BrClN_3O \cdot \frac{1}{2}H_2O$ | C: 60.74 / 60.78 | H: 5.29 / 5.31 | N: 7.87 / 7.41 |
| 39 | $CH_3$ | 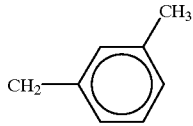 | 1 | Br | 224–226 | $C_{28}H_{30}BrN_3O \cdot 3/10H_2O$ | C: 65.96 / 66.01 | H: 6.05 / 5.96 | N: 8.24 / 8.17 |
| 40 | $CH_3$ |  | 1 | Br | 210–212 | $C_{28}H_{30}BrN_3O \cdot 3/10H_2O$ | C: 65.96 / 65.81 | H: 6.05 / 5.97 | N: 8.24 / 8.02 |
| 41 | $CH_3$ | 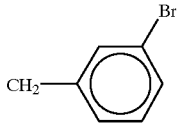 | 1 | Br | 240–242 | $C_{28}H_{30}BrN_3O \cdot 3/10H_2O$ | C: 65.96 / 66.00 | H: 6.05 / 6.09 | N: 8.24 / 8.28 |
| 42 | $CH_3$ | 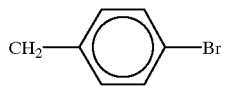 | 1 | Br | 205–206 | $C_{27}H_{27}Br_2N_3O$ | C: 56.96 / 56.74 | H: 4.78 / 4.91 | N: 7.38 / 7.60 |
| 43 | $CH_3$ | | 1 | Br | 219–221 | $C_{27}H_{27}Br_2N_3O \cdot \frac{3}{8}i\text{-}PrOH$ | C: 57.14 / 56.88 | H: 5.29 / 5.50 | N: 6.94 / 6.71 |

TABLE 7

| Example | R4 | R10 | m | z | Melting point(° C.) | Composition formula | Elemental analysis Calculated/analyzed | | |
|---|---|---|---|---|---|---|---|---|---|
| 44 | CH3 | 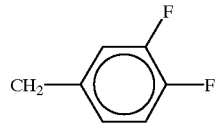 | 1 | Br | 139–141 | $C_{27}H_{26}F_2BrN_3O \cdot \frac{1}{2}EtOH$ | C: 61:21<br>61.34 | H: 5.32<br>5.52 | N: 7.65<br>7.38 |
| 45 | CH3 | 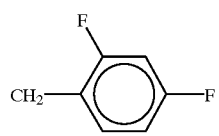 | 1 | Br | 206–208 | $C_{27}H_{26}F_2BrN_3O$ | C: 61.60<br>61.72 | H: 4.98<br>5.14 | N: 7.98<br>7.96 |
| 46 | CH3 | 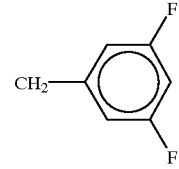 | 1 | Br | 225–262 | $C_{27}H_{26}F_2BrN_3O$ | C: 61.60<br>61.38 | H: 4.98<br>5.05 | N: 7.98<br>7.91 |
| 47 | CH3 | 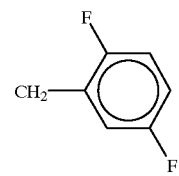 | 1 | Br | 215–217 | $C_{27}H_{26}F_2BrN_3O$ | C: 61.60<br>61.40 | H: 4.98<br>5.27 | N: 7.98<br>7.79 |
| 48 | CH3 | 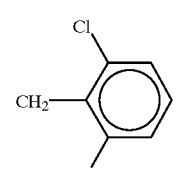 | 1 | Br | 273–275 | $C_{27}H_{26}BrCl_2N_3O$ | C: 57.98<br>57.91 | H: 4.69<br>4.75 | N: 7.51<br>7.74 |
| 49 | CH3 | 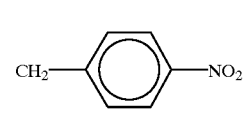 | 1 | Br | 215–217 | $C_{27}H_{27}BrN_4O_3$ | C: 60.57<br>60.56 | H: 5.08<br>5.19 | N: 10.46<br>10.34 |
| 50 | CH3 | 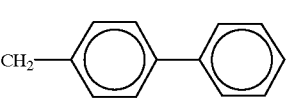 | 1 | Cl | 248–249 | $C_{33}H_{32}ClN_3O$ | C: 75.92<br>75.54 | H: 6.18<br>6.37 | N: 8.05<br>7.92 |
| 51 | CH3 | 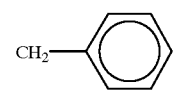 | 3 | Br | 155–157 | $C_{29}H_{32}BrN_3O \cdot \frac{1}{10}H_2O$ | C: 65.96<br>66.76 | H: 6.24<br>6.21 | N: 8.08<br>7.97 |
| 52 | CH3 | 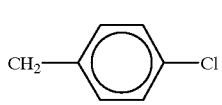 | 3 | Br | 205–207 | $C_{29}H_{31}BrClN_3O$ | C: 62.38<br>62.21 | H: 5.70<br>5.90 | N: 7.53<br>7.24 |
| 53 | CH3 | 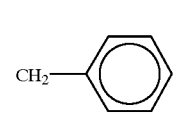 | 2 | Br | 171–173 | $C_{28}H_{30}BrN_3O \cdot \frac{1}{2}H_2O$ | C: 65.50<br>65.37 | H: 6.09<br>6.02 | N: 8.18<br>8.30 |

Experimental Example

1. Anticholinergic Action in Guinea-pig Ileum and Atria

Male Hartley guinea pigs were sacrificed by blowing on the head and bleeding.

Ileal segments (about 3 cm long) were suspended in organ baths containing Tyrode solution equilibrated with a mixture of 95% $O_2$ and 5% $CO_2$ at 32° C.

Responses to acetylchloline (ACh) added cumulatively to the baths were isotonically recorded under a tension of 1 g. Dose-response curves of ACh were determined in the absence and presence of test compounds in various concentrations added to the baths 5 min. before ACh application.

The affinity ($pA_2$) of test compounds for muscarinic receptor was determined according to Schild method (Arunlakshana, O. and Schild, H. O. (1959) Brit. J. Pharmacol., 14 48–58).

The isolated atria were suspended under 0.5 g tension in organ baths containing Tyrode solution gassed with 95% $O_2$ and 5% $CO_2$ at 32° C.

Dose-response curves were obtained by cumulative addition of ACh and repeated in the presence of various concentrations of test compounds, allowing 10 min. equilibration time.

The affinity of test compounds were determined as described for ileum. Results are shown in Table 8.

TABLE 8

| No. of examples | Anticholinergic activity ($pA_2$) | |
|---|---|---|
| | Ileum | Atrium |
| 7 | 8.95 | 8.21 |
| 8 | 8.17 | 7.08 |
| 11 | 10.16 | 8.88 |
| 14 | 9.17 | 7.73 |
| Atropine | 8.67 | 8.91 |
| Oxybutynin | 8.44 | 8.39 |

The compounds of the present invention had a high affinity for muscarinic receptors in guinia pig ileum but a much lower affinity for cardiac receptors.

In particular, the affinities obtained for compounds of Example 8, 11 and 14 were 10 times greater for receptors in ileum as compared to receptors in heart.

2. Effect on Rhythmic Bladder Contraction

Male Wistar rats were fixed in supine position under the halothane anesthesia and a balloon-tip catheter was inserted into the bladder through the small incision of apex opening a lower abdomen along the midline, followed by pursestring suture. The catheter was led out of upper end of abdominal incision sutured, connected with a pressure transducer.

The balloon was filled with about 0.1 to 0.3 ml of water. After the rhythmic contraction of the urinary bladder became constant at a threshold intravesical pressure, test compounds were given intraduodenally. The inhibitory effects were estimated by the reduction in amplitude of bladder contraction. The compounds of the present invention decreased in amplitude of bladder contraction at a dose of 0.03 mg/kg or more.

3. Effect on bethanechol-induced diarrhea

Test compounds were administered orally to male ICR mice and, 30 min. later 20 mg/kg of bethanechol were given subcutaneously. The appearance of diarrhea was observed from the administration of bethanechol until 0.5 hours later.

The compounds of the present invention show the inhibitory effects of a dose of 0.06 mg/kg or more.

4. Anticholinergic Action in Guinea-pig Trachea

Male Hartley guinea-pigs were killed by blowing on the head and bleeding.

Ring strips of trachea were suspended in organ bath filled with Tyrode solution, kept at 37° C. and gassed with a mixture of 95% $O_2$ and 5% $CO_2$.

Responses to ACh were isometrically recorded under a tension of 1 g. Concentration-Response curves were obtained cumulative addition of ACh and repeated in the presence of various concentrations of test compounds, allowing 10 minutes equilibration time.

The affinity ($pA_2$) of test compounds for muscarinic receptor was determined according to Schild method (Arunlakshana, O. and Schild, H. O. (1959), Brit. J. Pharmacol., 14 48–58) or van Rossum (van Rossum, J. M. (1963), Arch. Int. Pharmacodyn, Ther., 143 299–330). Results are shown in Table 9.

TABLE 9

| No. of examples | Anticholinergic activity ($pA_2$) | |
|---|---|---|
| | Trachea | Atrium |
| 44 | 8.28 | 7.54 |
| 50 | 8.34 | 7.52 |
| 51 | 8.34 | 7.70 |
| Ipratropium | 8.85 | 8.82 |

The affinities ($pA_2$) of the compounds of the present invention were significantly greater for muscarinic receptors in trachea as compared to receptors in heart.

Utilizability in the Industry

As descried above, the compounds of the present invention will be clinically useful in treating irritable bowel syndrome, dysuria such as pollakiuria and urinary incontinence and chronic respiratory obstructive diseases.

We claim:

1. An imidazole represented by formula (2)

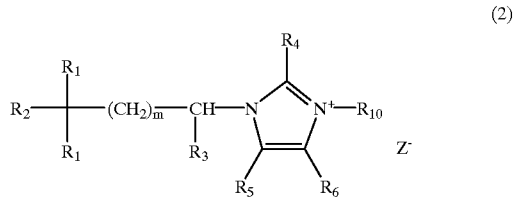

(2)

wherein $R_1$ is a phenyl group which may be optionally substituted with one or more substituents selected from the group consisting of halogen, lower alkyl group, lower alkoxy group, nitro group, and phenyl group, $R_2$ is a carboxyl group or $CONR_7R_8$ group wherein $R_7$ and $R_8$ are each independently hydrogen atoms or lower alkyl groups, $R_3$ is a hydrogen atom or a lower alkyl group, $R_4$, $R_5$ and $R_6$ are each independently hydrogen atoms, lower alkyl groups which may be independently optionally substituted with one or more substituents selected from the group consisting of halogen, lower alkoxy group, hydroxy group, and phenyl group, or $C_3$–$C_8$ cycloalkyl groups, $R_{10}$ is a lower alkyl group or an aralkyl group which may be optionally substituted with one or more substituents selected from the group consisting of halogen, lower alkyl group, lower alkoxy group, hydroxyl group, nitro group and phenyl group, and m denotes an integer from 1 to 6 and Z is a halogen atom.

2. A pharmaceutical composition, comprising:

an imidazole represented by formula (2)

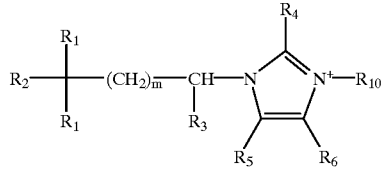

(2)

wherein $R_1$ is a phenyl group which may be optionally substituted with one or more substituents selected from the group consisting of halogen, lower alkyl group, lower alkoxy group, nitro group, and phenyl group, $R_2$ is a carboxyl group or $CONR_7R_8$ group wherein $R_7$ and $R_8$ are each independently hydrogen atoms or lower alkyl groups, $R_3$ is a hydrogen atom or a lower alkyl group, $R_4$, $R_5$ and $R_6$ are each independently hydrogen atoms, lower alkyl groups which may be independently optionally substituted with one or more substituents selected from the group consisting of halogen, lower alkoxy group, hydroxy group, and phenyl group, or $C_3$–$C_8$ cycloalkyl groups, $R_{10}$ is a lower alkyl group or an aralkyl group which may be optionally substituted with one or more substituents selected from the group consisting of halogen, lower alkyl group, lower alkoxy group, hydroxyl group, nitro group and phenyl group, and m denotes an integer from 1 to 6 and Z is a halogen atom, and an inert carrier.

3. A method for treating dysuria comprising:

administering, to a subject in need thereof, an effective amount of a composition comprising:

an imidazole represented by formula (2)

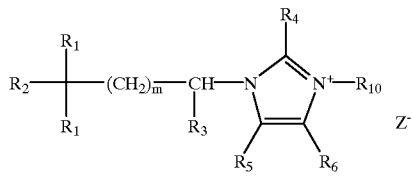

(2)

wherein $R_1$ is a phenyl group which may be optionally substituted with one or more substituents selected from the group consisting of halogen, lower alkyl group, lower alkoxy group, nitro group, and phenyl group, $R_2$ is a carboxyl group or $CONR_7R_8$ group wherein $R_7$ and $R_8$ are each independently hydrogen atoms or lower alkyl groups, $R_3$ is a hydrogen atom or a lower alkyl group, $R_4$, $R_5$ and $R_6$ are each independently hydrogen atoms, lower alkyl groups which may be independently optionally substituted with one or more substituents selected from the group consisting of halogen, lower alkoxy group, hydroxy group, and phenyl group, or $C_3$–$C_8$ cycloalkyl groups, $R_{10}$ is a lower alkyl group or an aralkyl group which may be optionally substituted with one or more substituents selected from the group consisting of halogen, lower alkyl group, lower alkoxy group, hydroxyl group, nitro group and phenyl group, and m denotes an integer from 1 to 6 and Z is a halogen atom, and an inert carrier.

* * * * *